(12) United States Patent
Buderer

(10) Patent No.: US 9,849,133 B2
(45) Date of Patent: Dec. 26, 2017

(54) PHARMACEUTICAL FORMULATIONS OF XANTHINE OR XANTHINE DERIVATIVES, AND THEIR USE

(71) Applicant: Imprimis Pharmaceuticals, Inc., San Diego, CA (US)

(72) Inventor: Matthew J. Buderer, Oak Harbor, OH (US)

(73) Assignee: Eton Pharmaceuticals, Inc., Deer Park, IL (US)

( * ) Notice: Subject to any disclaimer, the term of this patent is extended or adjusted under 35 U.S.C. 154(b) by 289 days.

(21) Appl. No.: 14/307,773

(22) Filed: Jun. 18, 2014

(65) Prior Publication Data

US 2015/0017151 A1    Jan. 15, 2015

Related U.S. Application Data

(60) Provisional application No. 61/836,535, filed on Jun. 18, 2013.

(51) Int. Cl.

| | | |
|---|---|---|
| *A61K 31/522* | (2006.01) | |
| *A61P 15/00* | (2006.01) | |
| *A61K 31/472* | (2006.01) | |
| *A61K 31/5575* | (2006.01) | |
| *A61K 31/417* | (2006.01) | |
| *A61K 9/00* | (2006.01) | |
| *A61K 45/06* | (2006.01) | |
| *A61K 38/48* | (2006.01) | |

(52) U.S. Cl.
CPC .......... *A61K 31/522* (2013.01); *A61K 9/0019* (2013.01); *A61K 9/0034* (2013.01); *A61K 31/417* (2013.01); *A61K 31/472* (2013.01); *A61K 31/5575* (2013.01); *A61K 38/4886* (2013.01); *A61K 45/06* (2013.01); *C12Y 304/24003* (2013.01)

(58) Field of Classification Search
CPC .............. A61K 2300/00; A61K 31/195; A61K 31/135; A61K 31/137; A61K 31/192; A61K 31/196; A61K 31/335; A61K 31/4045; A61K 31/485; A61K 31/167; A61K 31/18; A61K 31/351; A61K 31/65; A61K 31/19; A61K 31/245; A61K 31/407; A61K 31/417; A61K 31/472; A61K 31/522; A61K 31/5575; A61K 31/7048; A61K 45/06; A61K 38/12; A61K 38/4886; A61K 9/0014; A61K 9/00; A61K 9/0048; A61K 9/0019; A61K 9/0034; A61K 9/0031; A61K 9/0043; A61K 9/02; A61K 9/06; A61K 33/04; A61K 33/30; A61K 33/32; A61K 36/889; A61K 36/185; A61K 36/54; A61K 36/63; A61K 36/736; A61K 36/82; A61K 36/886; A61K 36/899; A61K 8/27; A61K 8/922; A61K 8/25; A61K 8/26; A61K 8/368; A61K 8/97; A61K 2800/31; A61K 2800/522; A61K 41/0004; A61K 47/14; A61K 47/20; A01N 43/54; A01N 43/78; A01N 37/18; A01N 59/16; A01N 65/00; A01N 65/22; A01N 65/40; A61Q 19/00; A61Q 19/001; C12Y 304/24003
See application file for complete search history.

(56) References Cited

U.S. PATENT DOCUMENTS

| | | |
|---|---|---|
| 4,191,748 A | 3/1980 | Holzman |
| 6,127,363 A | 10/2000 | Doherty, Jr. et al. |
| 8,133,903 B2 | 3/2012 | Gonzalez-Cadavid et al. |
| 2004/0087591 A1 | 5/2004 | Garvey et al. |
| 2005/0085486 A1 | 4/2005 | Gonzalez-Cadavid et al. |
| 2006/0292213 A1* | 12/2006 | Gerber ............... A61K 31/4166 424/451 |
| 2011/0243919 A1* | 10/2011 | Sabatino ............. A61K 38/4886 424/94.67 |

FOREIGN PATENT DOCUMENTS

WO    2002092097 A1    11/2002

OTHER PUBLICATIONS

Sigma-Aldrich "Collagenase from Clostridium histolyticum Type IA, crude, suitable for general use" Product Information: Collagenase (Cat. No. C9891), RMR,MAM , 2008 (02/08-1), pp. 1-3.*
Assoc. of Peyronie's Disease Advocates (APDA) "Treatment Comparison" <URL:www.peyroniesassociation.org/treatment/treatment-comparison/> archived May 5, 2012, accessed online Sep. 16, 2016, 2 pages.*
Ei-Sakka, A. "Reversion of Penile Fibrosis: Current Information and a New Horizon" Arab J. Urol., May 6, 2011, 9, pp. 49-55; doi:10.1016/j.aju.2011.03.013.*
Brant et al. 'Treatment of Peyronie's disease with oral pentoxifylline.' Nature Clinical Practice Urology. 2006, vol. 3, No. 2, pp. 111-115.
Smith et al. 'Pentoxifylline treatment and penile calcifications in men with Peyronie's disease.' Asian Journal of Andrology. 2011, vol. 13, No. 2, pp. 322.
Safarinejad et al. 'A double-blind placebo-controlled study of the efficacy and safety of pentoxifylline in early chronic Peyronie's disease.' BJU International. 2010, vol. 106, No. 2, pp. 240-248.
International Search Report and Written Opinion of the International Searching Authority for International Application No. PCT/US2014/042945, dated Oct. 10, 2014 (13 pages).

* cited by examiner

*Primary Examiner* — Christopher R Tate
*Assistant Examiner* — Aaron J Kosar
(74) *Attorney, Agent, or Firm* — Lathrop Gage LLP

(57) ABSTRACT

The present invention relates to pharmaceutical formulations comprising xanthine or xanthine derivatives, kits thereof, and methods for treating fibrotic diseases by local administration.

12 Claims, No Drawings

PHARMACEUTICAL FORMULATIONS OF XANTHINE OR XANTHINE DERIVATIVES, AND THEIR USE

CROSS-REFERENCE TO RELATED APPLICATIONS

This application claims priority under 35 U.S.C. §119(e) to U.S. Provisional Application No. 61/836,535 filed on Jun. 18, 2013 entitled "Pharmaceutical Formulations of Xanthine or Xanthine Derivatives, and Their Use" the entire contents of which is hereby incorporated by reference.

FIELD OF USE

The present disclosure relates to pharmaceutical formulations comprising xanthine or a xanthine derivative, such as pentoxifylline, and methods for treating a fibrotic disease, such as Peyronie's disease by local administration.

BACKGROUND OF THE INVENTION

Fibrotic diseases can be found in a variety of tissues. For example, Peyronie's disease (PD) is a fibromatosis (Hellstrom and Bivalacqua, 2000; Schwarzer et al., 2001; Jarow et al., 1997; Devine et al., 1997) of the tunica albuginea (TA), the specialized lining of the corpora cavernosa of the penis. Clinically, this usually leads to penile deformation (curved penis during erection), pain, and quite frequent erectile dysfunction. Fibrotic disease can also be found in other tissues, for example, pulmonary fibrosis, liver fibrosis, renal fibrosis, and vascular fibrosis.

It has been indicated that PD plaques and/or other fibrotic conditions can be pharmacologically arrested or reduced in size, by decreasing collagen synthesis and inducing myofibroblast apoptosis (Gonzalez-Cadavid et al., U.S. Pat. No. 8,133,903).

Oral administration of a nonspecific PDEi, e.g., pentoxifylline, has been suggested to be useful in reducing collagen levels in Peyronie's Disease plaques (Brant et al., Nature Clinical Practice Urology 2006, Vol 3, p. 111; Smith et al., Asian Journal of Andrology 2011, Vol 13, p. 322; Safarinejad et al., BJU International 2010, Vol 106, p. 240). However, oral pentoxifylline has been shown to have moderate to minimal improvement.

Therefore, there remains a need for treatment of fibrotic diseases, e.g., Peyronie's disease.

SUMMARY OF THE INVENTION

Provided herein are pharmaceutical formulations comprising xanthine or a xanthine derivative, such as pentoxifylline (1-(5-oxohexyl)-3,7-dimethylxanthine), kits thereof, and methods for treating a fibrotic disease by local administration.

In one aspect, provided herein is a pharmaceutical formulation comprising a therapeutically effective amount of a compound of formula I:

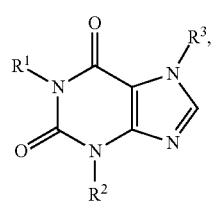

(I)

or a pharmaceutically acceptable salt, ester, amide or prodrug thereof, and a pharmaceutically acceptable excipient or carrier suitable for local administration, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted.

In another aspect, provided herein is a kit comprising:
a pharmaceutical formulation containing a therapeutically effective amount of a compound of formula I, or a pharmaceutically acceptable salt, ester, amide or prodrug thereof, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted;
an apparatus for locally administering the formulation;
a container for housing the formulation and the drug delivery apparatus; and
instructions for use.

In still another aspect, provided herein is a method for treating a fibrotic disease, e.g., Peyronie's disease, in a subject in need thereof, comprising locally administering to the subject a pharmaceutical formulation comprising a therapeutic effective amount of a compound of formula I, or a pharmaceutically acceptable salt thereof, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted.

$R^1$, $R^2$ and $R^3$ can be each, independently, H, or optionally substituted $C_1$-$C_6$ alkyl. In particular, $R^1$, $R^2$ and $R^3$ are each, independently, H, $C_1$-$C_6$ alkyl, or $C_1$-$C_6$ alkyl substituted with acyl.

The compound of formula I can be a nonspecific phosphodiesterase inhibitor (PDEi). The compound of formula I can also be selected from the group consisting of pentoxifylline, caffeine, theophylline, and aminophylline.

Also provided herein is a pharmaceutical formulation comprising, consisting essentially of, or consisting of a therapeutically effective amount of a nonspecific PDEi or a pharmaceutically acceptable salt, ester, amide or prodrug thereof, and a pharmaceutically acceptable excipient or carrier suitable for local administration.

In another aspect, provided herein is a kit comprising: a pharmaceutical formulation comprising, consisting essentially of, or consisting of a therapeutically effective amount of a nonspecific PDEi or a pharmaceutically acceptable salt, ester, amide or prodrug thereof; an apparatus for locally administering the formulation; a container for housing the formulation and the drug delivery apparatus; and instructions for use.

In yet another aspect, provided herein is a method for treating a fibrotic disease, e.g., Peyronie's disease, in a subject in need thereof, comprising locally administering to the subject a pharmaceutical formulation comprising, consisting essentially of, or consisting of a therapeutic effective amount of a nonspecific PDEi or a pharmaceutically acceptable salt thereof.

The nonspecific PDEi mentioned can be pentoxifylline, aminophylline, enprofylline, isbufylline, theophylline, theobromine, or 3-isobutyl-1-methylxanthine (IBMX).

In certain particular embodiments, the pharmaceutical formulation consists essentially of or consists of the therapeutically effective amount of pentoxifylline or a pharmaceutically acceptable salt thereof.

The fibrotic disease includes Peyronie's disease, Raynaud's syndrome, psoriasis plaques, eczema, and keloid scars. In certain particular embodiments, the fibrotic disease is Peyronie's disease or keloid scar.

In particular embodiments, the pharmaceutical formulations, kits thereof, and methods described above relate to treatment of Peyronie's disease or erectile dysfunction. The erectile dysfunction can be associated with Peyronie's disease.

In other embodiments, the pharmaceutical formulations, kits thereof, and methods described above relate to treatment of keloid scars in a subject in need thereof. The pharmaceutical formulation can comprise, consist essentially of, or consist of a nonspecific PDEi, e.g., pentoxifylline, and caffeine. The formulation can also comprise, consist essentially of, or consist of a nonspecific PDEi, e.g., pentoxifylline, and EGCG (green tea catechin). Furthermore, the formulation can comprise, consist essentially of, or consist of a nonspecific PDEi, e.g., pentoxifylline, and a mast cell stabilizer, e.g., tranilast. These formulations can be injected into the keloid scars.

The pharmaceutical formulation can further comprise a pharmaceutically acceptable excipient or carrier, including, but not limited to, an antioxidant, an adjuvant or synergist, and a preservative.

The pharmaceutical formulation can comprise an EDTA sodium salt. The EDTA sodium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

The pharmaceutical formulation can also comprise an EDTA magnesium salt. The EDTA magnesium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

The pharmaceutical formulation can further comprise ethanol. The ethanol can be 190 proof. The ethanol can be 0-15% by volume of the formulation, for example, 0, 1, 2, 3, 4, 5, 6, 7, 8, 9, 10, 11, 12, 13, 14, or 15% by volume of the formulation.

The pharmaceutical formulation can comprise benzyl alcohol. The benzyl alcohol can be 0-1.5% by weight of the formulation, for example, 0, 0.1, 0.2, 0.3, 0.4, 0.5, 0.6, 0.7, 0.8, 0.9, 1.0, 1.1, 1.2, 1.3, 1.4, or 1.5% by volume of the formulation.

The pharmaceutical formulation can be filtered before local administration, such as filtering through a 0.22 micron filter.

The pharmaceutical formulation has a pH of between 4 and 8. In particular embodiments, the pharmaceutical formulation has a pH of between 5.5 and 6. The pH can be adjusted by adding acids or bases, e.g., HCl or NaOH.

The therapeutic effective amount can be between 4 mg and 20 mg. In particular embodiments, the therapeutic effective amount is between 6 mg and 10 mg.

The pharmaceutical formulation can be administered one to four times in a twenty-four hour period. In particular embodiments, the pharmaceutical formulation is administered daily until desired effects are achieved.

The pharmaceutical formulation can comprise a unit dosage of the compound of formula I. In particular embodiments, the pharmaceutical formulation comprises a unit dosage of pentoxifylline.

The pharmaceutical formulation can be administered topically, transdermally, to the penis of the subject. In particular embodiments, the pharmaceutical formulation is administered by intracavernosal injection. Accordingly, the pharmaceutical formulation can comprise a sterile liquid composition and the pharmaceutically acceptable excipient or carrier is suitable for intracavernosal injection. In other embodiments, the pharmaceutically acceptable excipient or carrier is suitable for topical or transdermal administration, and the formulation comprises a composition to be applied to a body surface, such as an ointment, cream, gel or lotion.

In certain embodiments, the pharmaceutical formulation is not administered (e.g., intracavernosally injected) directly into the area of the fibrotic disease, e.g., the area of the Peyronie's disease. In certain particular embodiments for treating Peyronie's disease, the pharmaceutical formulation is administered (e.g., intracavernosally injected) at the base of the penis about 2 cm from where the penis attaches to the abdomen.

The pharmaceutical formulation can comprise a second active agent, including nitrovasodilators, alpha receptor blocking agents, ergot alkaloids, antihypertenseive agents, vasodilators, naturally occurring, semisynthetic and synthetic prostaglandins, and vasoactive intestinal peptides. The vasodilators can be alprostadil (Prostaglandin $E_1$), papaverine, and phentolamine.

In certain embodiments of the formulations, kits thereof, and methods for treating Peyronie's disease, the pharmaceutical formulation further comprises a collagenase, such as collagenase *clostridium histolyticum*, or Xiaflex®. In certain particular embodiments, the pharmaceutical formulation comprises, consists essentially of, or consists of pentoxifylline and a collagenase, e.g., collagenase *clostridium histolyticum* or Xiaflex®.

The formulations, kits thereof, and methods provided herein can be used as a mono therapy or a part of a combo therapy to treat a fibrotic disease, such as Peyronie's disease. For example, the formulation comprising the compound of formula I, e.g., pentoxifylline, can be used as a mono therapy or a part of a combo therapy. The formulation consisting essentially of or consisting of a nonspecific PDEi, e.g., pentoxifylline, can also be used as a mono therapy, or a part of a combo therapy, e.g., in combination with a collagenase therapy, such as collagenase *clostridium histolyticum* or Xiaflex®.

DETAILED DESCRIPTION

This disclosure relates to the finding that local administration of a xanthine derivative, e.g., pentoxifylline, has produced unexpected improvement in treating a fibrotic disease. For example, intracavernosal injection of a composition comprising pentoxifylline has resulted remarkable improvement to symptoms of PD, such as erectile dysfunction. Furthermore, intracavernosal injection of pentoxifylline has been found to produce fewer side effects.

Accordingly, provided herein are pharmaceutical formulations of xanthine or a xanthine derivative, such as pentoxifylline, kits thereof, and methods for treating a fibrotic disease by local administration.

Definitions

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a nonspecific phosphodiesterase inhibitor" includes a mixture of two or more nonspecific phosphodiesterase inhibitors, and reference to "an excipient or carrier" includes mixtures of two or more excipients or carriers, and the like.

In describing and claiming the present invention, the following terminology will be used in accordance with the definitions set out below.

"Alkyl" as used herein refers to a linear or branched saturated hydrocarbon group. Non-limiting examples of $C_1$-$C_6$ alkyl include methyl, ethyl, n-, and iso-propyl, n-, iso-, sec-, and t-butyl, n-pentyl, n-hexyl, 1,3-dimethylbutyl, 3,3-dimethylbutyl.

"Alkenyl" as used herein refers to an alkyl group with at least one double bond.

"Alkynyl" as used herein refers to an alkyl groups with at least one triple bond.

"Cycloalkyl" as used herein refers to a monocyclic or bicyclic saturated hydrocarbon group, including, but not limited to, cyclopropyl, cyclobutyl, cyclopentyl, and cyclohexanyl.

"Heterocyclyl" as used herein refers to a cycloalkyl group with at least one heteroatom, such as N, O, S, and P. Non-limiting examples of heterocyclyl include aziridinyl, azetidinyl, pyrrolidinyl and tetrahydrofuranyl.

"Aryl" as used herein refers to a monocyclic or a bicyclic aromatic hydrocarbon group, including, but not limited to, phenyl and naphthyl.

"Heteroaryl" as used herein refers to an aryl group with at least one heteroatom, such as, N, O, S, and P. Non-limiting examples of heteroaryl include pyrrolyl, imidazolyl, furanyl, pyridinyl, and pyrazinyl.

"Acyl" as used herein refers to a group of formula

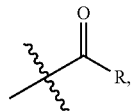

wherein R is alkyl, alkenyl, alkynyl, cycloalkyl, aryl, heterocyclyl, or heteroaryl, each of which can be optionally substituted.

The term "fibrotic disease" as used herein refers to conditions where the fibroproliferative response produces an abnormal accumulation of fibrocellular scar tissue that compromises the normal architecture and function of the affected tissue. Non-limiting examples of fibrotic disease include Peyronie's disease, Raynaud's syndrome, psoriasis plaques, eczema, keloid scars, pulmonary fibrosis, liver fibrosis, renal fibrosis, and vascular fibrosis.

The term "erectile dysfunction" is intended to include any and all types of erectile dysfunction, including: vasculogenic, neurogenic, endocrinologic and psychogenic impotence ("impotence" is used here in its broadest sense to indicate an inability a periodic or consistent inability to achieve or sustain an erection of sufficient rigidity for sexual intercourse; see U.S. Pat. No. 5,242,391); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, Disorders of Sexual Desire (New York, N.Y.: Brunner Mazel Book Inc., 1979)). Generally, however, the erectile dysfunction referred to herein is vasculogenic erectile dysfunction, particularly vasculogenic impotence.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a fibrotic disease, as the term is used herein, thus encompasses both prevention of the disorder in a predisposed individual and treatment of the disorder in a clinically symptomatic individual.

The term "phosphodiesterase inhibitor" as used herein is intended to mean an agent that is capable of inhibiting or selectively reducing the activity of any one or more phosphodiesterases.

The term "active agent" used herein refers to a chemical material or compound that induces a desired effect, e.g., reduction of fibrosis scars and/or improvement of other symptoms.

"Excipient or carrier" as used herein refers to excipients or carrier materials suitable for local drug administration. Excipient or carriers useful herein include any such material known in the art which is nontoxic and does not interact with other components of the composition in a deleterious manner.

By an "effective" amount of a drug or pharmacologically active agent is meant a nontoxic but sufficient amount of the drug or agent to provide the desired effect, e.g., reduction of fibrosis scars and/or improvement of other symptoms.

Additional pharmacologically active agents may be optionally delivered along with the primary active agent, i.e., the nonspecific phosphodiesterase inhibitor. Non-limiting examples of the active agent include nitrovasodilators, alpha receptor blocking agents, ergot alkaloids, antihypertensive agents, vasodilators, naturally occurring, semisynthetic and synthetic prostaglandins, and vasoactive intestinal peptide.

Non-limiting examples of nitrovasodilators include nitroglycerin, linsidomine such as insidomine chlorhydrate ("SIN-1"), molsidomine, organic nitrates such as isosorbide dinitrate, erythrityl tetranitrate and amyl nitrate, sodium nitroprusside, S-nitrosothiols such as S-nitroso-N-acetyl-d, 1-penicillamine ("SNAP"), S-nitroso-N-cysteine and S-nitroso-N-glutathione ("SNO-GLU"), and diazenium diolates ("NONOates") such as (Z)-1-{N-methyl-N-[6-(N-methylammoniohexyl)amino]}diazen-1-ium-1,2-diolate, (Z)-1-[N-(3-ammoniopropyl)-N-(n-propyl)amino]diazen-1-ium-1,2-diolate, (Z)-1-{N-[3-aminopropyl]-N-[4-(3-aminopropylammonio)butyl]amino}diazen-1-ium-1,2-diolate and sodium (Z)-1-(N,N-diethylamino)-diazen-1-ium-1,2-diolate.

Non-limiting examples of alpha receptor blocking agents include phenoxybenzamine, dibenamine, doxazosin, terazosin, phentolamine, tolazoline, prazosin, trimazosin, alffizosin, tamsulosin and indoramin.

Non-limiting examples of ergot alkaloids include ergotamine and ergotamine analogs, such as acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride.

Non-limiting examples of antihypertensive agents include diazoxide, hydralazine and minoxidil.

Non-limiting examples of vasodilators include nimodipine, pinacidil, cyclandelate and isoxsuprine.

Non-limiting examples of naturally occurring pro staglandins include $PGE_0$, $PGE_1$, PGA1, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$. Non-limiting examples of semisynthetic or synthetic derivatives of natural pro staglandins include carboprost tromethamine, dinoprost tromethamine, dinoprostone, lipoprost, gemeprost, metenoprost, sulprostone and tiaprost.

Non-limiting examples of nonspecific phosphodiesterase inhibitors include theophylline, theobromine, 3-isobutyl-1-methylxanthine (IBMX), and pentoxifylline.

In some embodiments, additional pharmacological agents that may be optionally delivered along with the primary active agent include anesthetic(s) (i.e., substances or compounds that induce insensitivity to pain such as a temporary loss of sensation). Those having ordinary skill in the art will select such anesthetic(s) and their concentrations, if desired. As a non-binding guideline only, the concentration of an anesthetic in the composition may be between about 0.1 mass % and about 0.5 mass %.

Non-limiting examples of acceptable anesthetics that may be so used include lidocaine, tetracaine, proparacaine, procaine or dyclonine.

Furthermore, if desired, other pharmacological agents, for example, without limitations, anti-bacterial agent(s) (i.e., antibiotics), antiviral medicament(s) or antifungal medicament(s), may be optionally additionally included for delivery along with the primary active agent. Those having ordinary skill in the art will select such additional agents and their concentration, if desired.

The active agents may be administered, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involve reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, ptoluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of acid moieties which may be present on a phosphodiesterase inhibitor molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

The terms "Local administration" and "locally administering" as used herein refer to treatment of a fibrotic disease by administering at sites approximate to local symptoms (e.g., PD plaques) of the fibrotic disease. It is distinguished from systemic administrations, such as oral administration or intravenous injection, wherein dosage of a pharmaceutical composition is relatively similar throughout the body of a subject. Non-limiting examples of local administration include intracavernosal injection, topical administration, and transdermal administration.

The term "intracavernosal" as used herein refers to an injection into one or both corpora of the corpora cavernosal tissues of the penis.

The term "transdermal" delivery includes both transdermal (or "percutaneous") and transmucosal administration, i.e., delivery by passage of a drug through the body surface, i.e., the skin or mucosal tissue. "Transdermal" delivery is also intended to encompass delivery of a drug by passage across scrotal tissue. Examples of conventional transdermal drug delivery systems include transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it can contain multiple reservoirs. The reservoir can comprise a polymeric matrix of a pharmaceutically acceptable contact adhesive material that serves to affix the system to the skin during drug delivery. Non-limiting examples of suitable skin contact adhesive materials include polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or hydrogel reservoir, or can take some other form.

The term "topical administration" is used in its conventional sense to mean delivery of a topical drug or pharmacologically active agent to the skin or mucosa. Examples of formulations for topical drug delivery include ointments and creams. Ointments are semisolid preparations which are typically based on petrolatum or other petroleum derivatives. Creams containing the selected active agent include viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Methods of Treatment

In one aspect, provided herein is a method for treating a fibrotic disease in a subject in need thereof, which comprises locally administering to the subject a pharmaceutical formulation comprising a therapeutic effective amount of a compound of formula I:

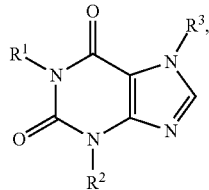

or a pharmaceutically acceptable salt thereof, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted.

In another aspect, provided herein is a method for treating Peyronie's disease in a subject in need thereof, which comprises locally administering to the subject a pharmaceutical formulation comprising a therapeutic effective amount of a compound of formula I:

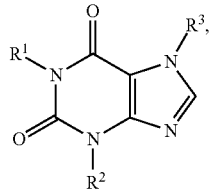

or a pharmaceutically acceptable salt thereof, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted.

In certain embodiments of the methods, $R^1$, $R^2$ and $R^3$ are each, independently, H, or optionally substituted $C_1$-$C_6$ alkyl.

In other embodiments, $R^1$, $R^2$ and $R^3$ are each, independently, H, $C_1$-$C_6$ alkyl, or $C_1$-$C_6$ alkyl substituted with acyl.

In still other embodiments, the compound of formula I is a nonspecific phosphodiesterase inhibitor (PDEi). In certain embodiments, the nonspecific PDEi is pentoxifylline, aminophylline, enprofylline, isbufylline, theophylline, theobromine, or 3-isobutyl-1-methylxanthine (IBMX).

In yet other embodiments, the compound of formula I is selected from the group consisting of pentoxifylline, caffeine, theophylline, and aminophylline.

In another aspect, provided herein is a method for treating a fibrotic disease in a subject in need thereof, which comprises locally administering to the subject a pharmaceutical formulation comprising, consisting essentially of or consisting of a therapeutic effective amount of a nonspecific PDEi or a pharmaceutically acceptable salt thereof, wherein the nonspecific PDEi is pentoxifylline, aminophylline, enprofylline, isbufylline, theophylline, theobromine, or 3-isobutyl-1-methylxanthine (IBMX).

In yet another aspect, provided herein is a method for treating Peyronie's disease in a subject in need thereof, which comprises injecting into at least one of the corpus cavernosa of the penis of the subject a pharmaceutical formulation comprising, consisting essentially of or consisting of a therapeutically effective amount of a nonspecific PDEi or a pharmaceutically acceptable salt thereof, wherein the nonspecific PDEi is pentoxifylline, aminophylline, enprofylline, isbufylline, theophylline, theobromine, or 3-isobutyl-1-methylxanthine (IBMX).

In particular embodiments of the methods provided above, the pharmaceutical formulation consists essentially of pentoxifylline or a pharmaceutically acceptable salt thereof.

The fibrotic disease includes Peyronie's disease, Raynaud's syndrome, psoriasis plaques, eczema, and keloid scars. In certain particular embodiments, the fibrotic disease is Peyronie's disease. In other embodiments, the fibrotic disease is keloid scar.

The treatment method leads to improvement of various fibrotic conditions, for example, reduction of fibrotic scars. In certain particular embodiments, the treatment of Peyronie's disease results in reduction of PD plaques. In other embodiments, the treatment results in improvement of erectile dysfunction. In certain embodiments, the erectile dysfunction is associated with PD.

In certain embodiments, the pharmaceutical formulation is administered locally to treat erectile dysfunction. In particular embodiments, the erectile dysfunction is associated with Peyronie's disease.

In certain embodiments of the methods for treating keloid scars in a subject in need thereof, the pharmaceutical formulation comprising, consisting essentially of or consisting of a nonspecific PDEi, e.g., pentoxifylline, and caffeine. In other embodiments, the formulation comprises, consists essentially of or consists of a nonspecific PDEi, e.g., pentoxifylline, and EGCG (green tea catechin). In still other embodiments, the formulation comprises, consists essentially of or consists of a nonspecific PDEi, e.g., pentoxifylline, and a mast cell stabilizer, e.g., tranilast. These formulations can be injected into the keloid scars. In certain embodiments, the pharmaceutical formulation further comprises a pharmaceutically acceptable excipient or carrier, including, but not limited to, an antioxidant, an adjuvant or synergist, and a preservative.

Non-limiting examples of the antioxidant are a-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, d-a-tocopherol natural, d-a-tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thio sulfate, thiourea, tocopherols.

Non-limiting examples of the adjuvant or synergist are citric acid, EDTA (ethylenediaminetetraacetate) and salts, hydroxyquinoline sulfate, phosphoric acid, and tartaric acid.

In particular embodiments, the pharmaceutical formulation further comprises an EDTA sodium salt. The EDTA sodium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

In particular embodiments, the pharmaceutical formulation further comprises an EDTA magnesium salt. The EDTA magnesium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

Non-limiting examples of the preservative are benzalkonium chloride, benzethonium chloride, benzoic acid and salts, benzyl alcohol, boric Acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol.

In particular embodiments, the pharmaceutical formulation further comprises ethanol. The ethanol can be 190 proof. The ethanol can be 0-15% by volume of the formulation, for example, 0, 1, 2, 3, 4, 5, 6, 7, 8, 9, 10, 11, 12, 13, 14, or 15% by volume of the formulation.

In other embodiments, the pharmaceutical formulation further comprises benzyl alcohol. The benzyl alcohol can be 0-1.5% by weight of the formulation, for example, 0, 0.1, 0.2, 0.3, 0.4, 0.5, 0.6, 0.7, 0.8, 0.9, 1.0, 1.1, 1.2, 1.3, 1.4, or 1.5% by volume of the formulation.

In other embodiments, the pharmaceutical formulation is filtered before local administration. In particular embodiments, the pharmaceutical formulation is filtered through a 0.22 micron filter before local administration.

In other embodiments, the pharmaceutical formulation has a pH of between 4 and 8. In particular embodiments, the pharmaceutical formulation has a pH of between 5.5 and 6. The pH can be adjusted by adding acids or bases, e.g., HCl or NaOH.

In other embodiments of the methods, the therapeutic effective amount is between 4 mg and 20 mg. In particular embodiments, the therapeutic effective amount is between 6 mg and 10 mg.

In other embodiments of the methods, the pharmaceutical formulation is administered one to four times in a twenty-four hour period. In particular embodiments, the pharmaceutical formulation is administered daily until desired effects are achieved.

In certain embodiments of the methods, the pharmaceutical formulation comprises a unit dosage of the compound of formula I. In particular embodiments, the pharmaceutical formulation comprises a unit dosage of pentoxifylline.

The pharmaceutical formulation can be administered to a subject in need thereof by various local administrations. In certain embodiments, the pharmaceutical formulation is administered topically. In other embodiments, the pharmaceutical formulation is administered transdermally. In still other embodiment, the pharmaceutical formulation is administered locally to the penis of the subject. In particular embodiments, the pharmaceutical formulation is administered by intracavernosal injection.

In certain particular embodiment, provided herein is a method for treating Peyronie's disease in a subject in need thereof, comprising injecting into at least one of the corpus cavernosa of the penis of the subject a pharmaceutical formulation consisting essentially of a therapeutic effective amount of pentoxifylline or a pharmaceutically acceptable salt thereof.

In certain embodiments of the methods, the pharmaceutical formulation is not administered (e.g., intracavernosally injected) directly into the area of the fibrotic disease. In particular embodiments of the methods for treating Peyronie's disease, the pharmaceutical formulation is not administered (e.g., intracavernosally injected) directly into the area of the Peyronie's disease. In other embodiments of the methods for treating Peyronie's disease, the pharmaceutical formulation is administered (e.g., intracavernosally injected) at the base of the penis about 2 cm from where the penis attaches to the abdomen.

In certain embodiments of the methods, the pharmaceutical formulation further comprises a second active agent. In particular embodiments, the second active agent is a vasodilator, e.g., alprostadil (Prostaglandin $E_1$), papaverine, and/or phentolamine. In other embodiments, the second active agent is a nonspecific phosphodiesterase inhibitor as defined above, e.g., pentoxifylline, aminophylline, enprofylline, isbufylline, theophylline, theobromine, and/or 3-isobutyl-1-methylxanthine (IBMX). In still other embodiments, the second active agent is selected from the group consisting of nitrovasodilators, alpha receptor blocking agents, ergot alkaloids, antihypertenseive agents, vasodilators, naturally occurring, semisynthetic and synthetic prostaglandins, and/or vasoactive intestinal peptide.

In other embodiments of the methods for treating Peyronie's disease, the pharmaceutical formulation further comprises a collagenase, such as collagenase *clostridium histolyticum*, or Xiaflex®. In certain particular embodiments, the pharmaceutical formulation comprises, consists essentially of or consists of pentoxifylline and a collagenase, e.g., collagenase *clostridium histolyticum* or Xiaflex®.

The methods provided herein can be used as a mono therapy or a part of a combo therapy. In certain embodiments, the formulation comprising the compound of formula I, e.g, pentoxifylline, is used as a mono therapy. In certain particular embodiments, the formulation consisting essentially of a nonspecific PDEi, e.g., pentoxifylline, is used as a mono therapy to treat a fibrotic disease, such as Peyronie's disease.

In other embodiments, the formulation comprising the compound of formula I, e.g, pentoxifylline, is used as a part of a combo therapy. In certain particular embodiments, the formulation consisting essentially of a nonspecific PDEi, e.g., pentoxifylline, is used to treat a fibrotic disease, such as Peyronie's disease, in combination with a collagenase therapy, e.g., collagenase *clostridium histolyticum* or Xiaflex®.

Pharmaceutical Formulation

In one aspect, provided herein is a pharmaceutical formulation comprising a therapeutically effective amount of a compound of formula I:

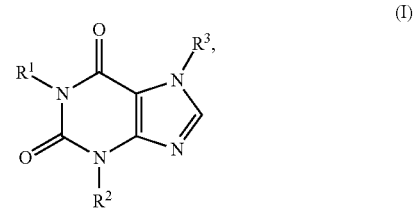

or a pharmaceutically acceptable salt, ester, amide or prodrug thereof, and a pharmaceutically acceptable excipient or carrier suitable for local administration, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted.

In one embodiment, $R^1$, $R^2$ and $R^3$ are each, independently, H, or optionally substituted $C_1$-$C_6$ alkyl.

In another embodiment, $R^1$ is $CH_3$—C(O)—$(CH_2)_4$ and each of $R^2$ and $R^3$ is $CH_3$.

In another embodiment, $R^1$, $R^2$ and $R^3$ are each, independently, H, $C_1$-$C_6$ alkyl, or $C_1$-$C_6$ alkyl substituted with acyl.

In still another embodiment, the compound of formula I is a nonspecific phosphodiesterase inhibitor (PDEi). In one embodiment, the nonspecific PDEi is pentoxifylline, aminophylline, enprofylline, isbufylline, theophylline, theobromine, or 3-isobutyl-1-methylxanthine (IBMX).

In yet another embodiment, the compound of formula I is selected from the group consisting of pentoxifylline, caffeine, theophylline, and aminophylline.

Also provided herein is a pharmaceutical formulation comprising, consisting essentially of or consisting of a therapeutically effective amount of a nonspecific PDEi or a pharmaceutically acceptable salt, ester, amide or prodrug thereof, and a pharmaceutically acceptable excipient or carrier suitable for local administration, wherein the nonspecific PDEi is pentoxifylline, aminophylline, enprofylline, isbufylline, theophylline, theobromine, or 3-isobutyl-1-methylxanthine (IBMX).

In certain particular embodiments, the pharmaceutical formulation comprises, consists essentially of or consists of a therapeutically effective amount of pentoxifylline or a pharmaceutically acceptable salt, ester, amide or prodrug thereof, and a pharmaceutically acceptable excipient or carrier suitable for local administration.

The formulations are useful in treating fibrotic diseases. The fibrotic diseases include Peyronie's disease, Raynaud's syndrome, psoriasis plaques, eczema, and keloid scars. In certain particular embodiments, the formulation is useful in treating Peyronie's disease. In other embodiments, the formulation is useful in treating keloid scars.

In certain embodiments, the pharmaceutical formulation results in improvement of fibrotic conditions, for example, reduction of fibrotic scars. In certain particular embodiments, the formulation reduces PD plaques. In other embodiments, the formulation results in improvement of erectile dysfunction. In certain embodiments, the erectile dysfunction is associated with PD.

In certain embodiments, the pharmaceutical formulation is administered locally to treat erectile dysfunction. In particular embodiments, the erectile dysfunction is associated with Peyronie's disease.

In certain embodiments of the formulations for treating keloid scars in a subject in need thereof, the pharmaceutical formulation consists essentially of a nonspecific PDEi, e.g., pentoxifylline, and caffeine. In other embodiments, the formulation consists essentially of a nonspecific PDEi, e.g., pentoxifylline, and EGCG. In still other embodiments, the formulation consists essentially of a nonspecific PDEi, e.g., pentoxifylline, and a mast cell stabilizer, e.g., tranilast. The formulations can be injected into the keloid scars.

The pharmaceutically acceptable excipient or carrier includes, but not limited to, an antioxidant, an adjuvant or synergist, and/or a preservative.

Non-limiting examples of the antioxidant are a-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, d-a-tocopherol natural, d-a-tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thio sulfate, thiourea, tocopherols.

Non-limiting examples of the adjuvant or synergist are citric acid, EDTA (ethylenediaminetetraacetate) and salts, hydroxyquinoline sulfate, phosphoric acid, and tartaric acid.

In particular embodiments, the pharmaceutical formulation further comprises an EDTA sodium salt. The EDTA sodium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

In particular embodiments, the pharmaceutical formulation further comprises an EDTA magnesium salt. The EDTA magnesium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

Non-limiting examples of the preservative are benzalkonium chloride, benzethonium chloride, benzoic acid and salts, benzyl alcohol, boric Acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol.

In particular embodiments, the pharmaceutical formulation further comprises ethanol. The ethanol can be 190 proof. The ethanol can be 0-15% by volume of the formulation, for example, 0, 1, 2, 3, 4, 5, 6, 7, 8, 9, 10, 11, 12, 13, 14, or 15% by volume of the formulation.

In other embodiments, the pharmaceutical formulation further comprises benzyl alcohol. The benzyl alcohol can be 0-1.5% by weight of the formulation, for example, 0, 0.1, 0.2, 0.3, 0.4, 0.5, 0.6, 0.7, 0.8, 0.9, 1.0, 1.1, 1.2, 1.3, 1.4, or 1.5% by volume of the formulation.

In other embodiments, the pharmaceutical formulation is filtered before local administration. In particular embodiments, the pharmaceutical formulation is filtered through a 0.22 micron filter before local administration.

In other embodiments, the pharmaceutical formulation has a pH of between 4 to 8. In particular embodiments, the pharmaceutical formulation has a pH of between 5.5 and 6. The pH can be adjusted to 5.5-6 by adding acids or bases, e.g., HCl or NaOH.

In other embodiments of the pharmaceutical formulations, the therapeutic effective amount is between 4 mg and 20 mg. In particular embodiments, the therapeutic effective amount is between 6 mg and 10 mg.

In other embodiments, the pharmaceutical formulation is administered one to four times in a twenty-four hour period. In particular embodiments, the pharmaceutical formulation is administered daily until desired effects are achieved.

In certain embodiments, the pharmaceutical formulation comprises a unit dosage of the compound of formula I. In particular embodiments, the pharmaceutical formulation comprises a unit dosage of pentoxifylline.

The pharmaceutical formulation can be administered to a subject in need thereof by various local administration, e.g., intracavernosal injection, topical administration, and transdermal administration. In particular embodiments, the pharmaceutical formulation comprises a sterile liquid composition and the pharmaceutically acceptable excipient or carrier is suitable for intracavernosal injection. In other embodiments, the pharmaceutical formulation is suitable for topical or transdermal administration. In certain particular embodiments, the pharmaceutical formulation comprises a composition to be applied to a body surface, and the pharmaceutically acceptable excipient or carrier is suitable for topical or transdermal administration. In certain embodiments, the pharmaceutical composition is an ointment, cream, gel or lotion.

In certain embodiments, the pharmaceutical formulation is not administered (e.g., intracavernosally injected) directly into the area of the fibrotic disease. In particular embodiments of the pharmaceutical formulations, the pharmaceutical formulation is not administered (e.g., intracavernosally injected) directly into the area of the Peyronie's disease. In other embodiments of the pharmaceutical formulations, the pharmaceutical formulation is administered (e.g., intracavernosally injected) at the base of the penis about 2 cm from where the penis attaches to the abdomen.

In certain embodiments, the pharmaceutical formulation further comprises a second active agent. In particular embodiments, the second active agent is a vasodilator, e.g., alprostadil (Prostaglandin $E_1$), papaverine, and/or phentolamine. In other embodiments, the second active agent is a nonspecific phosphodiesterase inhibitor as defined above, e.g., pentoxifylline, aminophylline, enprofylline, isbufylline, theophylline, theobromine, and/or 3-isobutyl-1-methylxanthine (IBMX). In still other embodiments, the second active agent is selected from the group consisting of nitrovasodilators, alpha receptor blocking agents, ergot alkaloids, antihypertenseive agents, vasodilators, naturally occurring, semisynthetic and synthetic prostaglandins, and/or vasoactive intestinal peptide.

In other embodiments, the pharmaceutical formulation further comprises a collagenase, such as collagenase *clostridium histolyticum* or Xiaflex®. In certain particular embodiments, the pharmaceutical formulation comprises, consists essentially of or consists of pentoxifylline and a collagenase, e.g., collagenase *clostridium histolyticum* or Xiaflex®.

The pharmaceutical formulations provided herein can be used as a mono therapy or a part of a combo therapy. In certain embodiments, the pharmaceutical formulation comprising the compound of formula I, e.g, pentoxifylline, is used as a mono therapy. In certain particular embodiments, the pharmaceutical formulation consisting essentially of a nonspecific PDEi, e.g., pentoxifylline, is used as a mono therapy to treat a fibrotic disease, such as PD.

In other embodiments, the formulation comprising the compound of formula I, e.g, pentoxifylline, is used as a part of a combo therapy. In certain embodiments, the formulation consisting essentially of a nonspecific PDEi, e.g., pentoxifylline, is used to treat a fibrotic disease, such as Peyronie's disease, in combination with a collagenase therapy, e.g., collagenase *clostridium histolyticum* or Xiaflex®.

In one particular embodiment, provided herein is a pharmaceutical formulation consisting essentially of a therapeutically effective amount of pentoxifylline or a pharmaceutically acceptable salt thereof, and a pharmaceutically acceptable excipient or carrier suitable for intracavernosal administration.

Kit

In one aspect, provided herein is a kit comprising: a pharmaceutical formulation containing a therapeutically effective amount of a compound of formula I:

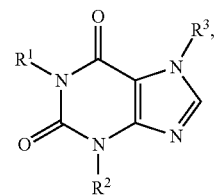

or a pharmaceutically acceptable salt, ester, amide or prodrug thereof, wherein $R^1$, $R^2$ and $R^3$ are each, independently, H, $C_1$-$C_6$ alkyl, $C_2$-$C_6$ alkenyl, $C_2$-$C_6$ alkynyl, cycloalkyl, heterocyclyl, aryl, or heteroaryl, each of which is optionally substituted;

an apparatus for locally administering the formulation;

a container for housing the formulation and the drug delivery apparatus; and instructions for use.

In one embodiment, $R^1$, $R^2$ and $R^3$ are each, independently, H, or optionally substituted $C_1$-$C_6$ alkyl.

In another embodiment, $R^1$, $R^2$ and $R^3$ are each, independently, H, $C_1$-$C_6$ alkyl, or $C_1$-$C_6$ alkyl substituted with acyl.

In still another embodiment, the compound of formula I is a nonspecific phosphodiesterase inhibitor (PDEi). In one embodiment, the nonspecific PDEi is pentoxifylline, aminophylline, enprofylline, isbufylline, theophylline, theobromine, or 3-isobutyl-1-methylxanthine (IBMX).

In yet another embodiment, the compound of formula I is selected from the group consisting of pentoxifylline, caffeine, theophylline, and aminophylline.

In another aspect, provided herein is a kit comprising: a pharmaceutical formulation comprising, consisting essentially of or consisting of a therapeutically effective amount of a nonspecific PDEi or a pharmaceutically acceptable salt, ester, amide or prodrug thereof, wherein the nonspecific PDEi is pentoxifylline, aminophylline, enprofylline, isbufylline, theophylline, theobromine, or 3-isobutyl-1-methylxanthine (IBMX); an apparatus for locally administering the formulation; a container for housing the formulation and the drug delivery apparatus; and instructions for use.

In certain particular embodiments, the pharmaceutical formulation comprises, consists essentially of or consists of a therapeutically effective amount of pentoxifylline or a pharmaceutically acceptable salt, ester, amide or prodrug thereof.

In certain embodiments, the kits are used to treat a fibrotic disease. Non-limiting examples of the fibrotic disease include Peyronie's disease, Raynaud's syndrome, psoriasis plaques, eczema, and keloid scars. In particular embodiments, the fibrotic disease is Peyronie's disease. In other embodiments, the fibrotic disease is keloid scars.

In other embodiments of the kits, the pharmaceutical formulation results in improvement of fibrotic conditions, for example, reduction of fibrotic plaques. In particular embodiments, the formulation reduces PD plaques. In other embodiments, the formulation improves erectile dysfunction. In certain embodiments, the erectile dysfunction is associated with PD.

In other embodiments of the kits, the pharmaceutical formulation is administered locally to treat erectile dysfunction. In particular embodiments, the erectile dysfunction is associated with Peyronie's disease.

In certain embodiments of the formulations for treating keloid scars in a subject in need thereof, the pharmaceutical formulation comprises, consists essentially of or consists of a nonspecific PDEi, e.g., pentoxifylline, and caffeine. In other embodiments, the formulation comprises, consists essentially of or consists of a nonspecific PDEi, e.g., pentoxifylline, and EGCG. In still other embodiments, the formulation comprises, consists essentially of or consists of a nonspecific PDEi, e.g., pentoxifylline, and a mast cell stabilizer, e.g., tranilast. The formulations can be injected into the keloid scars.

In certain embodiments, the pharmaceutical formulation further comprises a pharmaceutically acceptable excipient or carrier, including, but not limited to, an antioxidant, an adjuvant or synergist, and a preservative.

Non-limiting examples of the antioxidant are a-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, d-a-tocopherol natural, d-a-tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thio sulfate, thiourea, tocopherols.

Non-limiting examples of the adjuvant or synergist are citric acid, EDTA (ethylenediaminetetraacetate) and salts, hydroxyquinoline sulfate, phosphoric acid, and tartaric acid.

In particular embodiments, the pharmaceutical formulation further comprises an EDTA sodium salt. The EDTA sodium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

In particular embodiments, the pharmaceutical formulation further comprises an EDTA magnesium salt. The EDTA magnesium salt can be 0-0.15% by weight of the formulation, for example, 0.01, 0.02, 0.03, 0.04, 0.05, 0.06, 0.07, 0.08, 0.09, 0.10, 0.11, 0.12, 0.13, 0.14, or 0.15% by weight of the formulation.

Non-limiting examples of the preservative are benzalkonium chloride, benzethonium chloride, benzoic acid and salts, benzyl alcohol, boric Acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol. The benzyl alcohol can be 0-1.5% by weight of the formulation, for example, 0, 0.1, 0.2, 0.3, 0.4, 0.5, 0.6, 0.7, 0.8, 0.9, 1.0, 1.1, 1.2, 1.3, 1.4, or 1.5% by volume of the formulation.

In particular embodiments, the pharmaceutical formulation further comprises ethanol. The ethanol can be 190 proof. The ethanol can be 0-15% by volume of the formulation, for example, 0, 1, 2, 3, 4, 5, 6, 7, 8, 9, 10, 11, 12, 13, 14, or 15% by volume of the formulation.

In still other embodiments of the kits, the therapeutically effective amount is between 4 mg and 20 mg. In particular embodiments, the therapeutically effective amount is between 6 mg and 10 mg.

In certain embodiments, the pharmaceutical formulation is administered one to four times in a twenty-four hour period. In other embodiments, the pharmaceutical formulation is administered daily until desired effects are achieved.

In still other embodiments, the pharmaceutical formulation is filtered through a 0.22 micron filter. In particular embodiments, the pharmaceutical formulation is to be filtered through a 0.22 micron filter before administration.

In other embodiments, the pharmaceutical formulation has a pH of between 4 and 8. In particular embodiments, the pharmaceutical formulation has a pH of between 5.5 and 6. The pH can be adjusted to 5.5-6 before administration by adding acids or bases, e.g., HCl or NaOH.

Furthermore, the pharmaceutical formulation is administered locally. In certain embodiments, the pharmaceutical formulation comprises a sterile liquid composition and the pharmaceutically acceptable excipient or carrier is suitable for intracavernosal injection. In other embodiments, the pharmaceutical formulation comprises an ointment, cream, gel, or lotion, and the pharmaceutical acceptable excipient or carrier is suitable for topical or transdermal administration.

In certain particular embodiments, the pharmaceutical formulation consists essentially of a therapeutically effective amount of pentoxifylline or a pharmaceutically acceptable salt thereof, and a pharmaceutically acceptable excipient or carrier suitable for intracavernosal administration.

In certain embodiments, the pharmaceutical formulation is not administered (e.g., intracavernosally injected) directly into the area of the fibrotic disease. In particular embodiments, the pharmaceutical formulation is not administered (e.g., intracavernosally injected) directly into the area of the Peyronie's disease. In other embodiments, the pharmaceutical formulation is administered (e.g., intracavernosally injected) at the base of the penis about 2 cm from where the penis attaches to the abdomen.

In certain embodiments of the kits, the pharmaceutical formulation further comprises a second active agent. In particular embodiments, the second active agent is a vasodilator, e.g., alprostadil (Prostaglandin $E_1$), papaverine, and/or phentolamine. In other embodiments, the second active agent is a nonspecific phosphodiesterase inhibitor as defined above, e.g., pentoxifylline, aminophylline, enprofylline, isbufylline, theophylline, theobromine, and/or 3-isobutyl-1-methylxanthine (IBMX). In still other embodiments, the second active agent is selected from the group consisting of nitrovasodilators, alpha receptor blocking agents, ergot alkaloids, antihypertenseive agents, vasodilators, naturally occurring, semisynthetic and synthetic pro staglandins, and/or vasoactive intestinal peptide.

In other embodiments, the pharmaceutical formulation further comprises a collagenase, such as collagenase *clostridium histolyticum*, or Xiaflex®. In certain particular embodiments, the pharmaceutical formulation consists essentially of pentoxifylline and a collagenase, e.g., collagenase *clostridium histolyticum* or Xiaflex®.

In certain embodiments, the pharmaceutical formulation comprising the compound of formula I, e.g., pentoxifylline, is used as a mono therapy. In certain particular embodiments, the pharmaceutical formulation consisting essentially of a nonspecific PDEi, e.g., pentoxifylline, is used as a mono therapy to treat a fibrotic disease, such as Peyronie's disease.

In other embodiments, the formulation comprising the compound of formula I, e.g., pentoxifylline, is used as a part of a combo therapy. In certain embodiments, the formulation consisting essentially of a nonspecific PDEi, e.g., pentoxifylline, is used to treat a fibrotic disease, such as Peyronie's disease, in combination with a collagenase therapy, e.g., collagenase *clostridium histolyticum* or Xiaflex®.

The following examples are provided to further elucidate the advantages and features of the present invention, but are not intended to limit the scope of the invention. The examples are for the illustrative purposes only. USP pharmaceutical grade products were used in preparing the formulations described below.

EXAMPLES

Example 1

Preparing Pentoxifylline Formulations

Several pentoxifylline formulations were prepared using the compounds described in Table 1 in the quantities shown:

TABLE 1

| | |
|---|---|
| Formulation 1 | 1. Pentoxifylline 2% (active)<br>2. Ethanol 10% (cosolvent)<br>3. Edetate Disodium 0.1% (antioxidant/preservative)<br>4. Benzyl Alcohol 0.9% (preservative)<br>5. Hydrochloric Acid qs (pH adjustment/buffer)<br>6. Sodium Hydroxide qs (pH adjustment/buffer)<br>7. Water for injection qs ad |
| Formulation 2 | 1. Pentoxifylline 0.1%-2.5%<br>2. Ethanol 0.1%-10%<br>3. Edetate Disodium 0.02%-0.1%<br>4. Benzyl Alcohol 0.9%<br>5. Hydrochloric Acid qs or citric acid qs<br>6. Sodium Hydroxide qs or sodium citrate qs<br>7. Water for injection qs ad |
| Formulation 3 | 1. Pentoxifylline 2%<br>2. Propylene glycol 0.5%-5%<br>3. Edetate Disodium 0.1%<br>4. Benzyl Alcohol 0.9%<br>5. Hydrochloric Acid qs<br>6. Sodium Hydroxide qs<br>7. Water for injection qs ad |
| Formulation 4 | 1. Pentoxifylline 2%<br>2. Ethanol 10%<br>3. Edetate Disodium 0.1%<br>4. Benzyl Alcohol 0.9% or benzalkonium chloride 0.005-0.02% or hydroxyquinoline sulfate 0.005%-0.01%<br>5. Hydrochloric Acid qs<br>6. Sodium Hydroxide qs<br>7. Water for injection qs ad |
| Formulation 5 | 1. Pentoxifylline 2%<br>2. No cosolvent<br>3. No Antioxidant<br>4. Benzyl Alcohol 0.9% or any preservative<br>5. Hydrochloric Acid or citric acid qs<br>6. Sodium Hydroxide or sodium citrate qs<br>7. Water for injection qs ad |
| Formulation 9 | 1. Alprostadil 0.005%<br>2. Papaverine 3%<br>3. Phentolamine 0.3%<br>4. Pentoxifylline 0.6%<br>5. Ethanol 10%<br>3. Edetate Disodium 0.1%<br>4. Benzyl Alcohol 0.9%<br>5. Hydrochloric Acid qs or citric acid qs<br>6. Sodium Hydroxide qs or sodium citrate qs<br>7. Water for injection qs ad |

Example 2

Preparing a Caffeine Formulation

A formulation was prepared using the compounds described in Table 2 in the quantities shown:

TABLE 2

| | |
|---|---|
| Formulation 6 | 1. Caffeine 0.1-2.5% (as caffeine base or caffeine citrate) (active)<br>2. Ethanol 10% (cosolvent)<br>3. Edetate Disodium 0.1% (antioxidant/preservative)<br>4. Benzyl Alcohol 0.9% (preservative)<br>5. Hydrochloric Acid qs or citric acid (pH adjustment/buffer)<br>6. Sodium Hydroxide qs or sodium citrate (pH adjustment/buffer)<br>7. Water for injection qs ad |

Example 3

Preparing Aminophylline and Theophylline Formulations

The following formulations were prepared using the compounds described in Table 3 in the quantities shown:

TABLE 3

| | |
|---|---|
| Formulation 7 | 1. Aminophylline 0.1-2.5% (active)<br>2. Ethanol 10% (cosolvent)<br>3. Edetate Disodium 0.1% (antioxidant/preservative)<br>4. Benzyl Alcohol 0.9% (preservative)<br>5. Hydrochloric Acid qs or citric acid (pH adjustment/buffer)<br>6. Sodium Hydroxide qs or sodium citrate (pH adjustment/buffer)<br>7. Water for injection qs ad |
| Formulation 8 | 1. Theophylline 0.1-2.5% (active)<br>2. Ethanol 10% (cosolvent)<br>3. Edetate Disodium 0.1% (antioxidant/preservative)<br>4. Benzyl Alcohol 0.9% (preservative)<br>5. Hydrochloric Acid qs or citric acid (pH adjustment/buffer)<br>6. Sodium Hydroxide qs or sodium citrate (pH adjustment/buffer)<br>7. Water for injection qs ad |

Examples 4-6

Intracavernosal Injections of a Pentoxifylline Formulation

In Example 4, a 63 year old male with erectile dysfunction found that a combination of three vasoactive drugs: phentolamine, alprostadil, and papaverine, had no effect on his erectile dysfunction. A new injection was reformulated to contain the 3 vasoactive drugs mentioned above along with the addition of pentoxifylline, and was administered to the patient.

Various combined strengths of phentolamine, alprtostadil, papaverine and pentoxifylline were used in an attempt to improve his erectile dysfunction without demonstrable effects. However, the patient did notice remarkable improvement at a pentoxifylline dose of 4 mg per injection. The improvement was more remarkable at a 6 mg dose.

In Examples 5 and 6, patients suffering from Peyronie's disease were treated. A therapy cycle included injections of sterile pentoxifylline, more specifically, 6 separate injections to be conducted over every two weeks; the dosage was 5 mg of pentoxifylline in 1 ml volume, single use vials will be dispensed. The injections were made using a 21 gauge cannula directly into the Peyronie's plaque. A nerve block was done around injection site to lessen the pain. Manual manipulation and traction techniques were employed to massage the area of the injection. Patients returned after two weeks for another injection and manual manipulation session. Baseline measurements were collected before any treatment occurs to characterize the extent of the patient's disease. The degree of curvature was noted, as well as any pain/discomfort that the patient presently had and current sexual ability. Psychosocial effects related to the patient's disease were observed as well.

In Example 5, the patient suffering from Peyronie's disease was brought to the procedure room, prepared and draped in the usual sterile fashion. As a baseline characteristic of the disease state, the patient had penile curvature of 40 degrees dorsal and the location of the Peyronie's plaque was at dorsal and mid-shaft.

A total of 1 mL of 1% lidocaine was used to perform a local block. Once the patient was anesthetized, the plaque was isolated between two fingers and 1 mL of 5 mg Pentoxyfilline was injected into the plaque in a fan-like fashion. The patient tolerated the procedure well. The patient held pressure at the site of injection, and a light compressive dressing was applied. The patient was instructed to keep the dressing in place for three hours and then remove it. He was further instructed not to have sexual intercourse or masturbate for 24 hours.

In Example 6, another the patient suffering from Peyronie's disease was treated in the same fashion as the patient in Example 5. As a baseline characteristic of the disease state, the patient had penile curvature of 40 degrees dorsal and the location of the Peyronie's plaque was at dorsal and distal 2×1.

The patient tolerated the procedure well and received the same instructions as the patient in Example 5.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

Although the invention has been described with reference to the above examples, it will be understood that modifications and variations are encompassed within the spirit and scope of the invention. Accordingly, the invention is limited only by the following claims.

The invention claimed is:

1. A method for treating Peyronie's disease in a subject in need thereof, comprising injecting into at least one of the corpus cavernosa of the penis of the subject a pharmaceutical formulation consisting essentially of a therapeutic effective amount of pentoxifylline or a pharmaceutically acceptable salt thereof, wherein the formulation is used as a mono therapy for treating Peyronie's disease.

2. The method of claim 1, wherein the pharmaceutical formulation has a pH between 5.5 and 6.

3. The method of claim 1, wherein the therapeutically effective amount is between 4 mg and 20 mg per day.

4. The method of claim 1, wherein the pharmaceutical formulation is injected at the base of the penis about 2 cm from where the penis attaches to the abdomen.

5. The method of claim 1, wherein at least one symptom of Peyronie's disease is improved.

6. The method of claim 5, wherein the at least one symptom is pain.

7. The method of claim 5, wherein the at least one symptom is penile curvature.

8. The method of claim 5, wherein the at least one symptom is erectile dysfunction.

9. The method of claim 3, wherein at least one symptom of Peyronie's disease is improved.

10. The method of claim 9, wherein the at least one symptom is pain.

11. The method of claim 9, wherein the at least one symptom is penile curvature.

12. The method of claim 9, wherein the at least one symptom is erectile dysfunction.

* * * * *